United States Patent
Munson, Jr. et al.

(10) Patent No.: US 7,833,463 B1
(45) Date of Patent: Nov. 16, 2010

(54) SYSTEM AND METHOD FOR REMOVING AN ORGANIC FILM FROM A SELECTED PORTION OF AN IMPLANTABLE MEDICAL DEVICE USING AN INFRARED LASER

(75) Inventors: John Connell Munson, Jr., McKinney, TX (US); Jeffery Lee Green, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 1123 days.

(21) Appl. No.: 11/457,918

(22) Filed: Jul. 17, 2006

Related U.S. Application Data

(60) Provisional application No. 60/700,437, filed on Jul. 18, 2005.

(51) Int. Cl.
    *B23K 26/36* (2006.01)
    *B32B 38/10* (2006.01)
    *A61L 27/28* (2006.01)

(52) U.S. Cl. .................. 264/400; 156/344; 600/373; 264/482

(58) Field of Classification Search .............. 264/400, 264/482; 156/272.8, 344; 977/889; 600/373
    See application file for complete search history.

(56) References Cited

U.S. PATENT DOCUMENTS

| | | | | |
|---|---|---|---|---|
| 4,537,809 A | * | 8/1985 | Ang et al. | 428/42.2 |
| 5,534,094 A | * | 7/1996 | Arjavalingam et al. | 156/155 |
| 6,231,566 B1 | * | 5/2001 | Lai | 606/5 |
| 6,254,634 B1 | * | 7/2001 | Anderson et al. | 623/1.42 |
| 6,299,604 B1 | * | 10/2001 | Ragheb et al. | 604/265 |
| 2001/0026309 A1 | * | 10/2001 | Takeyama | 347/224 |
| 2004/0063805 A1 | * | 4/2004 | Pacetti et al. | 523/113 |
| 2005/0019371 A1 | * | 1/2005 | Anderson et al. | 424/426 |

OTHER PUBLICATIONS

TRUMPF Laser Marking Systems, Brochure, TRUMPH Inc. Farmington, CT, http://www.us.trumph.com.

* cited by examiner

*Primary Examiner*—Matthew J. Daniels
(74) *Attorney, Agent, or Firm*—Christopher S. L. Crawford; Peter Lando; Melissa Acosta

(57) ABSTRACT

In one embodiment, a method of removing an organic film from a selected portion of an implantable medical device includes: selecting a portion of an implantable medical device from which to remove an organic film comprising a silane primer and a polymer of para-xylylene; using a laser set at a first value for an operational parameter, tracing the perimeter of the selected portion to ablate the organic film along the perimeter; using an infrared laser set at a second value for the operational parameter, scanning the selected portion of the device to heat the surface of the device within the perimeter of the selected portion and thereby separate the organic film from the surface of the device within the perimeter of the selected portion; and mechanically removing the chemically separated organic film from the surface of the device within the perimeter to expose the selected portion.

8 Claims, 3 Drawing Sheets

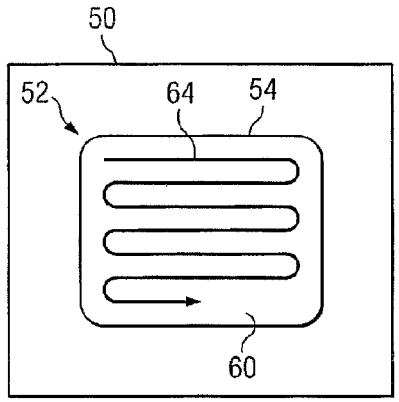
*FIG. 2C*
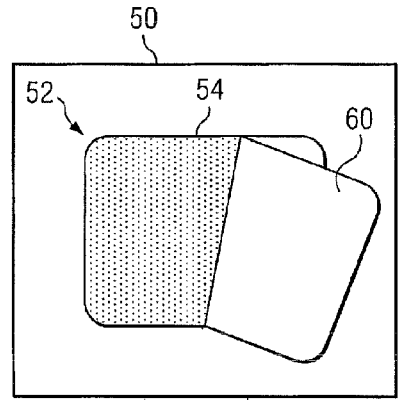
*FIG. 2D*
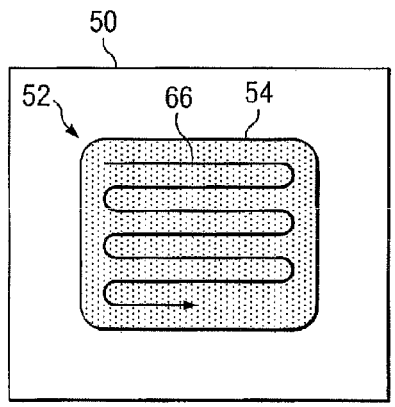
*FIG. 2E*
| ABLATING ORGANIC FILM | | | |
|---|---|---|---|
| | HIGH | TARGET | LOW |
| PULSE FREQUENCY (kHz) | 25 | 16 | 11 |
| VELOCITY (in/sec) | 100 | 100 | 100 |
| TRACK WIDTH (in) | .039 | .007 | .002 |
| POWER (%) | 100 | 100 | 80 |
*FIG. 3A*

| SCANNING SUBSTRATE TO SEPARATE ORGANIC FILM | | | |
|---|---|---|---|
| | HIGH | TARGET | LOW |
| PULSE FREQUENCY (kHz) | 60 | 60 | 25 |
| VELOCITY (in/sec) | 55 | 55 | 55 |
| TRACK WIDTH (in) | .039 | .002 | .002 |
| POWER (%) | 100 | 100 | 80 |

| CLEANING SURFACE OF SUBSTRATE | | | |
|---|---|---|---|
| | HIGH | TARGET | LOW |
| PULSE FREQUENCY (kHz) | 35 | 30 | 25 |
| VELOCITY (in/sec) | 55 | 55 | 55 |
| TRACK WIDTH (in) | .039 | .004 | .002 |
| POWER (%) | 100 | 100 | 100 |

SYSTEM AND METHOD FOR REMOVING AN ORGANIC FILM FROM A SELECTED PORTION OF AN IMPLANTABLE MEDICAL DEVICE USING AN INFRARED LASER

CROSS-REFERENCE TO RELATED APPLICATION

The present application claims the benefit of U.S. Provisional Application Ser. No. 60/700,437, entitled "SYSTEM AND METHOD FOR REMOVING AN ORGANIC FILM FROM A SELECTED PORTION OF AN IMPLANTABLE MEDICAL DEVICE USING AN INFRARED LASER," filed Jul. 18, 2005 which is incorporated herein by reference.

TECHNICAL FIELD

This application relates generally to manufacturing implantable medical devices and in particular to a system and method for removing an organic film from a selected portion of an implantable medical device using an infrared laser.

BACKGROUND

Organic film is used in various industries as a coating for devices. A thin film of organic material may serve one or more of numerous purposes. For example an organic film may have dielectric properties and substantially reduce the conduction of electric current. As another example, an organic film may serve to seal a device from moisture or corrosive chemicals. One such organic film is Parylene. Parylene is a polymer of para-xylylene that is commercially produced in various grades. When Parylene is applied to a metallic substrate, it is typically done using a two-step process. First, a thin primer layer is applied to the substrate. Then, the Parylene is applied using a vapor-phase deposition process. In this process, a di-para-xylylene dimer is placed in a vacuum system and heated to form a para-xylylene monomer vapor. The monomer vapor is then allowed to pass over the substrate at a lower temperature. At the lower temperature, the monomer vapor polymerizes on the substrate to form a uniform film.

Once the organic film has been applied to the substrate, it is sometimes beneficial to remove the organic film from selected portions of the substrate. For example, it is known to remove a portion of an organic film from an implantable pulse generator to form an electrode for the generator. Common techniques for removing the organic film involve the use of lasers to ablate the film covering the entirety of the selected portions. These ablation techniques typically involve the use of quad yttrium-aluminum-garnet (YAG) laser systems or eximer laser systems. The laser systems typically used to ablate these organic films generally utilize ultraviolet lasers. Such lasers have been utilized because, for example, organic films such as Parylene may have high absorption rates for ultraviolet wavelengths. By absorbing the energy transmitted from an ultraviolet laser, the efficiency of the film ablation is improved. In contrast, organic films such as Parylene may be substantially transparent to visible and infrared light. Existing techniques utilizing quad YAG laser systems and eximer laser systems can be prohibitively expensive. In some situations, plasma etching systems with infrared lasers have been used for ablation. Although, using existing techniques, such plasma etching systems produce inconsistent results with excessive processing times. Such inconsistent results and processing times are often not conducive to a production environment.

SUMMARY

Certain embodiments may reduce or eliminate certain problems and disadvantages associated with previous techniques for removing an organic film from a selected portion of an implantable medical device.

In some representative embodiments, a process is employed to remove a portion of organic film from a substrate using a relatively low cost laser. For example, a single pulsed YAG laser may be used to remove the organic film. The relatively low cost laser emits a laser pulse that is substantially transparent to the organic film. The laser pulse is converted to thermal energy by the substrate to which the organic film is bonded. The thermal energy is used to vaporize or ablate a portion of the organic film. Also, the thermal energy is used to break the chemical bonds between a primer substance and the surface of the substrate. Specifically, in some embodiments, the relatively low cost laser is operated using a first set of parameters to vaporize or ablate a perimeter path of the portion of the organic film to be removed. Using a second set of parameters, the laser is used to break the chemical bonds associated with a primer substance within the ablated path thereby enabling the remaining portion of organic film to be mechanical separated from the substrate.

Particular embodiments may provide one or more technical advantages. For example, certain embodiments provide techniques for removing an organic film from a selected portion of an implantable medical device using less expensive infrared laser systems than have been used with previous techniques. As another example, certain embodiments provide techniques for removing an organic film from a selected portion of an implantable medical device that require less time and provide more consistent results than previous techniques. Certain embodiments may provide all, some, or none of these advantages. Certain embodiments may provide one or more other technical advantages one or more of which may be readily apparent to those skilled in the art from the figures, descriptions, and claims included herein.

BRIEF DESCRIPTION OF THE DRAWINGS

FIGS. 2A-2E illustrate example steps for removing an organic film from a selected portion of a substrate according to one representative embodiment.

FIGS. 3A-3C illustrate example operational parameters and associated values for a laser used to remove an organic film from a selected portion of a substrate according to one representative embodiment.

FIG. 4 illustrates an example method of removing an organic film from a selected portion of a substrate according to one representative embodiment.

DESCRIPTION OF EXAMPLE EMBODIMENTS

In some representative embodiments, systems and methods are employed to remove a portion of organic film from a substrate (e.g., an implantable medical device). Certain organic films are substantially transparent to certain wavelengths of light and substantially opaque to other wavelengths of light. Certain of these organic films are applied to a substrate using a two-step process. First, a thin primer layer is applied to the substrate, forming a chemical bond with the substrate. Then, a polymer is applied to the substrate, forming a chemical bond with the primer. In certain embodiments, by utilizing a laser producing light that is not absorbed by the organic film, the energy from the laser may be allowed to heat the surface of the substrate to a temperature at which the chemical bonds between the substrate and the primer are broken. Once the chemical bonds have been broken, the separated portion of the organic film may be mechanically removed from the substrate.

Certain embodiments provide a system and method for removing an organic film from a selected portions of an implantable medical device using one or more infrared lasers. According to one embodiment, a method of removing an organic film from a selected portion of an implantable medical device, comprises: using an infrared laser set at a first value for an operational parameter, tracing the perimeter of the selected portion of the implantable medical device to ablate the organic film along the perimeter of the selected portion, wherein the organic film comprises a polymer bonded to the implantable medical device with a primer compound and the polymer substantially transmits infrared radiation; using an infrared laser set at a second value for the operational parameter, scanning the selected portion of the implantable medical device to heat the surface of the device within the perimeter of the selected portion and thereby separate the organic film from the surface of the device within the perimeter of the selected portion; and mechanically removing the chemically separated organic film from the surface of the implantable medical device within the perimeter of the selected portion of the device to expose the selected portion.

Figure 1:
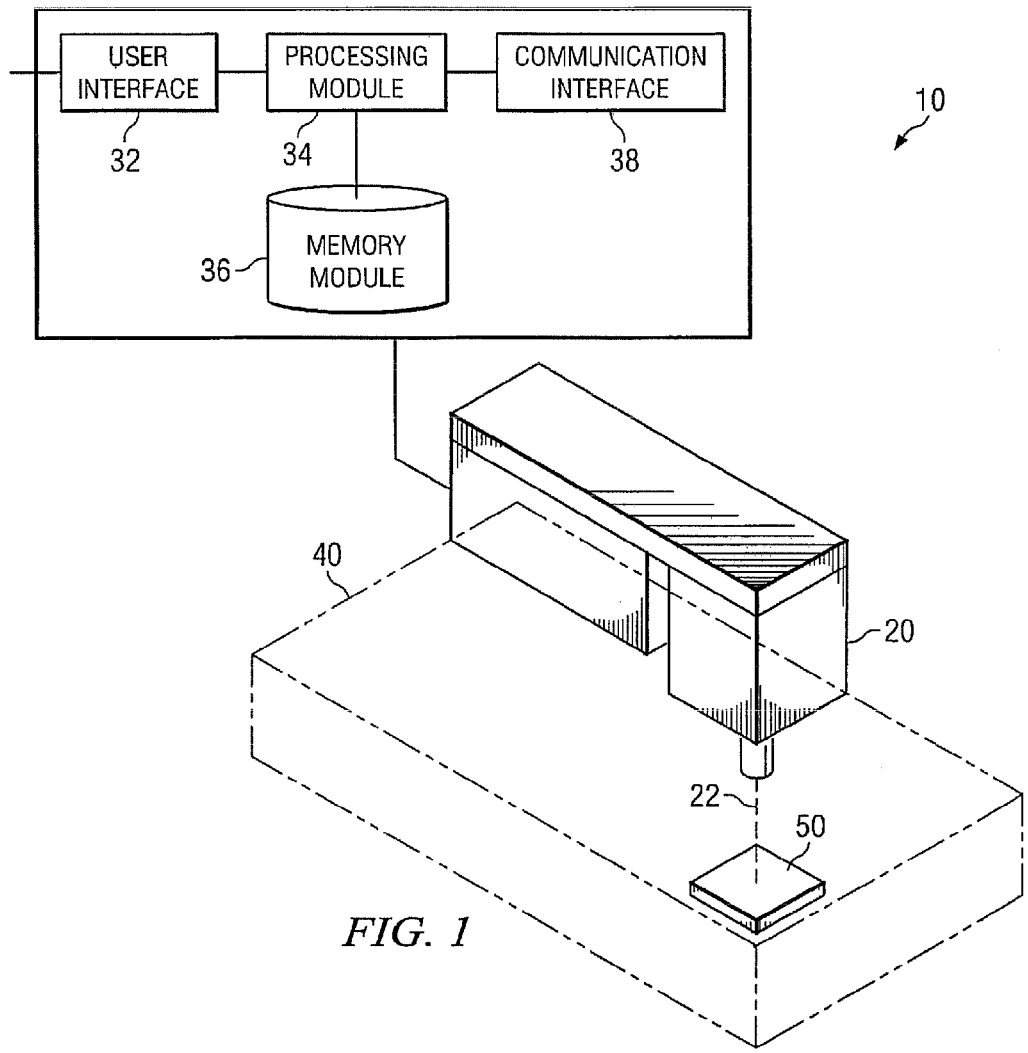
FIG. 1 illustrates an example embodiment of a system for removing an organic film from a selected portion of a substrate.

FIG. 1 illustrates an example embodiment of a system, indicated generally at 10, for removing an organic film from a selected portion of substrate 50. For example, system 10 may utilize an infrared laser to remove an organic film from a selected portion of an implantable medical device, such as an implantable pulse generator for neurostimulation. In certain embodiments, the organic film may include a silane primer and a polymer of para-xylylene, such as poly-monochloro-para-xylylene. In a particular embodiment, the organic film may be applied in a two-stage process with the silane primer being applied to form a chemical bond with the substrate before the polymer of para-xylylene is applied. For example, the silane primer may be applied by dipping the substrate into an aqueous alcohol silane solution. As another example, a silane primer may be applied by wiping or spraying a silane solution onto the substrate. After the silane primer has cured, the polymer of para-xylylene may be applied using a vapor-phase-deposition process to form a chemical bond with the silane primer.

In the embodiment illustrated, system 10 includes laser 20, laser control module 30, and support fixture 40. These components operate together to enable the removal of an organic film from a substrate 50. For example, laser 20, controlled by laser control module 30, may direct laser beam 22 at substrate 50 to remove the organic film covering a selected portion of substrate 50, while substrate 50 is being supported by support fixture 40.

Laser 20 may be an industrial laser that may be controlled to direct a laser beam at an object. Although laser 20 may emit a laser beam 22 in any suitable wavelength, in certain embodiments laser 20 emits laser beam 22 in the infrared spectrum which is substantially transmitted by typical organic films. The infrared spectrum generally comprises those wavelengths between the red end of the visible spectrum and the microwave spectrum, or wavelengths in the range of approximately 700 nanometers to approximately 1 millimeter. Additionally, in certain embodiments, system 10 may utilize more than one laser 20 and, in these embodiments, each laser 20 may or may not be the same or similar.

Although laser 20 may be any appropriate laser operating at any appropriate wavelength, in certain embodiments laser 20 may be selected such that the organic film covering substrate 50 is substantially transparent to laser beam 22 emitted from laser 20. In certain embodiments, laser 20 may be selected such that when operating at specified values for certain operational parameters, the resulting energy density is low enough not to damage the surface of substrate 50, but high enough to heat the surface of substrate 50 to a temperature sufficient to break the chemical bonds between the organic film and substrate 50. In a particular embodiment, this involves heating the surface of substrate 50 to a temperature sufficient to break the chemical bonds between a silane primer and substrate 50, which may be in excess of 250 degrees Celsius. In certain embodiments, laser 20 may be a may be a single pulsed yttrium-aluminum-garnet (YAG) laser operating at a wavelength of approximately 1064 nanometers. For example, laser 20 may be included in a VectorMark® etching system marketed and sold by TRUMPF Laser Marking Systems AG.

Laser control module 30 is coupled to laser 20 to allow for communication between laser control module 30 and laser 20. Laser control module 30 may be included within the same housing as laser 20 or may be located in a housing separate and distinct from laser 20. In the embodiment illustrated, laser control module 30 includes user interface 32, processing module 34, memory module 36, and communications interface 38. These components operate together to receive information from a system user, to control the operational parameters of laser 20, and to control the path of laser beam 22. Although these components are provided as representative examples, any appropriate components may be employed to provide the described functionality.

User interface 32 communicates information to and receives information from a system user. In certain embodiments, these communications may be transmitted to or received from one or more peripheral devices coupled to user interface 32. For example, user interface 32 may be coupled to a keyboard, mouse, touch pad, and/or monitor. Thus, user interface 32 includes any suitable hardware and/or controlling logic for communicating information to and from a system user with or without the use of one or more peripheral devices.

Communications interface 38 communicates information to, and may receive information from, one or more lasers 20. In certain embodiments, the information may be communicated wirelessly, using one or more wireless transmission protocols, or through a hardwired connection. For example, communications interface 38 may communicate certain operational parameters values and laser beam paths to laser 20 using a hardwired connection with an RS-232 connector. Thus, communication interface 38 includes any suitable hardware and/or controlling logic used for communicating information to laser 20. In certain embodiments, communications interface 38 and user interface 32 may be combined into a single device. In certain embodiments, one or more of communications interfaces 38 and user interfaces 32 may be distributed across multiple devices.

Processing module 34 controls the operation and administration of elements within laser control module 30 by processing information received from user interface 32, communications interface 38, and/or memory module 36. For example, processing module 34 may receive information from user interface 32, store information in memory module 36, and send information to communications interface 38. Accordingly, processing module 34 may include any hardware and/or controlling logic elements for controlling and processing information. For example, processing module 34 may be a programmable logic device, a microcontroller, and/or any other suitable processing device or group of devices.

Memory module 36 stores, either permanently or temporarily, data and other information for processing by processing module 34 and communication by user interface 32 and/or communication interface 38. For example, memory module 36 may store operational parameter values and/or laser beam path data for laser 20. Memory module 36 may include any one or a combination of volatile or nonvolatile local or remote devices suitable for storing information. For example, memory module 36 may include random access memory (RAM), read only memory (ROM), magnetic storage devices, optical storage devices, or any other suitable storage device or combination of these devices.

Support fixture 40 represents a surface for supporting substrate 50 while laser beam 22 is directed at a selected portion of substrate 50. In certain embodiments, support fixture 40 may include a clamping device, a T-slot table, a rotary indexing table, or a customized holding fixture. In other embodiments, support fixture 40 may be a pallet that allows substrate 50 to be properly positioned and held in place by gravity. Support fixture 40 may be a separate component or support fixture 40 may be integrally attached to a laser workstation housing laser 20 and/or laser control module 30. In certain embodiments, support fixture 40 may be positioned inside an enclosed work area while laser 20 is in operation.

Substrate 50 represents an object or a portion of an object on which an organic film has been applied. Substrate 50 may include one or more of numerous organic or inorganic materials. For example, substrate 50 may include a metallic substance such as an alloy of titanium. In certain embodiments, substrate 50 may be an electronic device such as an integrated circuit or a medical device such as an implantable medical device. For example, substrate 50 may be an implantable pulse generator (IPG) used for neurostimulation.

Figure 2A:
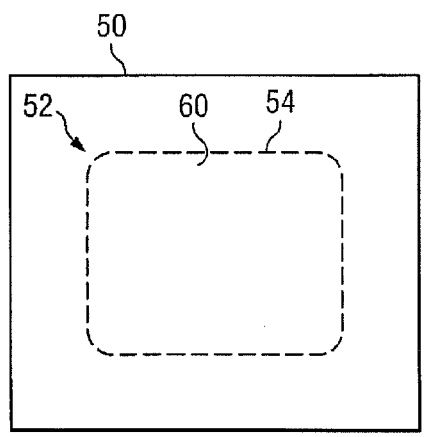

FIGS. 2A-2E illustrate example steps for removing an organic film from a selected portion of substrate 50. FIG. 2A illustrates substrate 50 and organic film 60 covering selected portion 52 of substrate 50. In certain embodiments, data defining selected portion 52 may be stored in memory module 36. The data may define the perimeter 54 of selected portion 52. The data may be stored in any appropriate format. In the embodiment illustrated, selected portion 52 is substantially rectangular in shape; however, in other embodiments, selected portion 52 may have any appropriate shape.

Figure 2B:
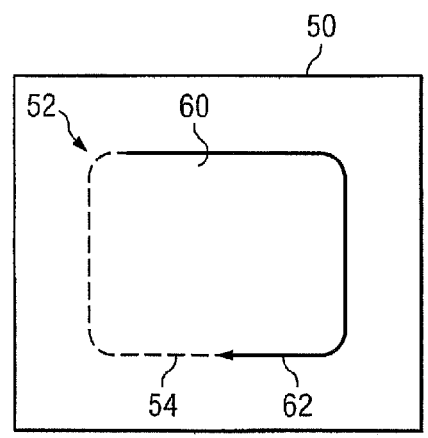

FIG. 2B illustrates an example perimeter path 62 that laser 20 may trace to ablate organic film 60 along perimeter 54 of selected portion 52. In operation, laser 20 may utilize a first value for an operational parameter when laser 20 traces perimeter path 62. Example operational parameters and associated values for use during this ablation procedure are discussed below with reference to FIG. 3A.

FIG. 2C illustrates an example scanning path 64 that laser 20 may scan to heat the surface of substrate 50 within perimeter 54 of selected portion 52 to separate organic film 60 from selected portion 52. In the embodiment illustrated, scanning path 64 includes a "zig-zag" path; however, in other embodiments, scanning path 64 may include a "spiral" path or any other appropriate path to heat the surface of substrate 50 within perimeter 54. In operation, laser 20 may utilize a second set of operational parameter values when laser 20 scans scanning path 64. Example operational parameters and associated values for use during this heating procedure are discussed below with reference to FIG. 3B.

FIG. 2D illustrates mechanical removal of organic film 60 covering selected portion 52 of substrate 50 within perimeter 54. In certain embodiments, organic film 60 may be peeled away from selected portion 52. For example, organic film 60 may be peeled away manually, using forced air, water, or other fluid, and/or using a device such as tweezers to lift the edge of organic film 60 and separate it from selected portion 52. Mechanically removing organic film 60 from selected portion 52 exposes the surface of selected portion 52 within perimeter 54.

FIG. 2E illustrates an example scanning path 66 that laser 20 may follow to clean the surface of substrate 50 within perimeter 54 of selected portion 52. In certain embodiments, the use of scanning path 66 to clean the surface of substrate 50 may provide a more aesthetically pleasing appearance of selected portion 52. For example, by utilizing scanning path 66, the surface of selected portion 52 may appear brighter, shinier, and/or cleaner than it would otherwise appear. As with scanning path 64, in the embodiment illustrated, scanning path 66 includes a "zig-zag" path; however, in other embodiments, scanning path 66 may include a "spiral" path or any other appropriate path to clean the surface of selected portion 52 within perimeter 54. In operation, laser 20 may utilize a third set of operational parameter values when laser 20 scans scanning path 66 to clean the surface of substrate 50. Example operational parameters and associated values for use during cleaning are discussed below with reference to FIG. 3C.

Although certain of the steps illustrated in FIGS. 2A-2E must necessarily precede other steps, other steps may be performed in a different order. For example, in certain embodiments, scanning selected portion 52 of substrate 50 to heat the surface of substrate 50 within perimeter 54 of selected portion 52 may occur prior to the ablation of organic film 60 along perimeter 54 of selected portion 52. As another example, laser control module 30 may control the operational parameters and laser beam path such that the ablation and heating steps occur during the same program using a single laser beam path, portions of the path involving ablation along perimeter 54 in connection with a first set of operational parameter values and portions of the path involving scanning within perimeter 54 in connection with a second set of operational parameter values. Additionally, in certain embodiments certain steps illustrated in FIGS. 2A-2E may be omitted and in certain embodiments other steps may be added.

Figures 3B, 3C, 4:
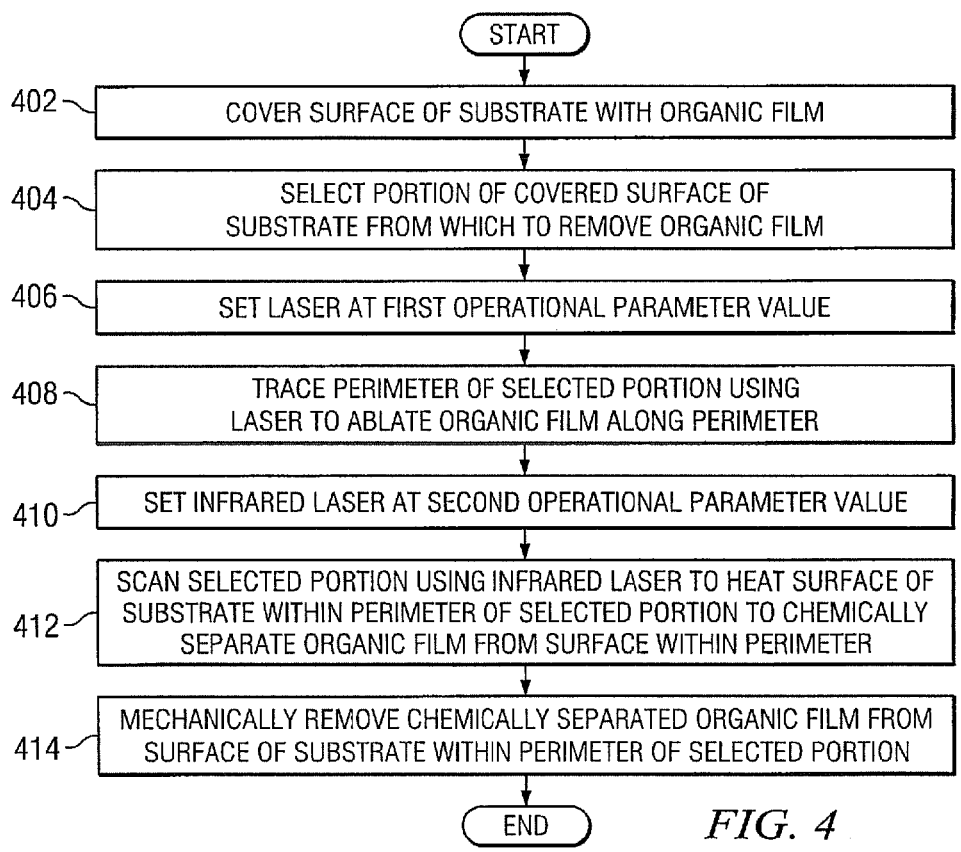

FIGS. 3A-3C illustrate example operational parameters and associated values for laser 20 used to remove organic film 60 from selected portion 52 of substrate 50. In particular embodiments, the example operational parameter values illustrated in FIGS. 3A-3C may be utilized by a single pulsed YAG laser operating at a wavelength of approximately 1064 nanometers to remove an organic film 60 including a silane primer and a polymer of para-xyxlylene from a substrate 50 including a titanium alloy.

FIG. 3A illustrates example operational parameter values, shown generally at 100, for use during ablation of selected portion 52 of substrate 50. Column 102 identifies example operational parameters. Columns 104, 106, and 108 identify example high, target, and low values, respectively, that may be used with laser 20. Rows 112, 114, 116, and 118 represent example operational parameters and associated example values. For example, cell 120 identifies 16 kilohertz as an example target pulse frequency for use with laser 20 to ablate organic film 60 from selected portion 52.

Similarly, FIGS. 3B and 3C illustrate example operational values, shown generally at 200 and 300, for heating the surface of substrate 50 to separate organic film 60 from selected portion 52 of substrate 50 and for cleaning the surface of selected portion 52 of substrate 50, respectively. For example, cell 220 identifies 60 kilohertz as an example target pulse frequency for use with laser 20 to heat the surface of substrate 50 to chemically separate organic film 60 from selected portion 52 of substrate 50. As another example, cell 320 identifies 30 kilohertz as an example target pulse frequency for use with laser 20 to clean the surface of selected portion 52 of substrate 50.

Although FIGS. 3A-3C provide example ranges of operational parameter values for laser 20, in certain embodiments laser 20 may operate at other operational parameter values to achieve the removal of organic film 60 from selected portion 52 of substrate 50. Additionally, in certain embodiments, other operational parameters not shown in FIGS. 3A-3C may be adjusted to optimize the performance of laser 20 for use in removing organic film 60 from selected portion 52 of substrate 50.

FIG. 4 illustrates an example method, shown generally at 400, for removing organic film 60 from selected portion 52 of substrate 50. At step 402, a surface of substrate 50 is covered with organic film 60. In certain embodiments, covering the surface may include applying a primer and utilizing a vapor-phase-deposition process to apply a polymer. In a particular embodiment, the primer may include a silane primer, such as gamma-methacryloxypropyltrimethoxysilane, and the polymer may include a polymer of para-xylylene, such as poly-monochloro-para-xylylene. At step 404, a portion 54 of the covered surface of substrate 50 is selected from which to remove organic film 60. In certain embodiments, data defining selected portion 52 is stored in memory module 36, accessed by processing module 34, and utilized by laser control module 30 to control laser 20. In a particular embodiment, data defining selected portion 52 is communicated to laser control module 30 by a system user, through the use of user interface 32.

At step 406, laser 20 is set at a first value for an operational parameter. In certain embodiments, the first operational parameter value may be included within operational parameter values 100, shown in FIG. 3A. In a particular embodiment, the first operational parameter value includes a pulse frequency of 16 kilohertz. At step 408, perimeter 54 of selected portion 52 is traced using laser 20 to ablate organic film 60 along perimeter 54 of selected portion 52. In certain embodiments, steps 406 and 408 may be performed using a laser 20 operating at any appropriate wavelength, including a wavelength in the ultraviolet or infrared spectrum.

At step 410, infrared laser 20 is set at a second value for the operational parameter. In certain embodiments, the second operational parameter value may be included within operational parameters 200, shown in FIG. 3B. In a particular embodiment, the second operational parameter value includes a pulse frequency of 60 kilohertz. At step 412, selected portion 52 is scanned using laser 20 to heat the surface of substrate 50 within perimeter 54 of selected portion 52 to separate organic film 60 from the surface of substrate 52 within perimeter 54 of selected portion 52. In certain embodiments, the surface may be heated to a temperature sufficient to break the bonds between a silane primer and substrate 50. In particular embodiments, the surface may be heated to a temperature of approximately 250 degrees Celsius. In certain embodiments, steps 410 and 412 may be performed using a laser 20 operating at any appropriate wavelength in the infrared spectrum. In a particular embodiment, laser 20 operates at a wavelength in the range of approximately 800-1600 nanometers. For example, steps 410 and 412 may be performed using a laser 20 emitting a laser beam 22 at a wavelength of approximately 1064 nanometers.

At step 414, separated organic film 60 is mechanically removed from the surface of substrate 50 within perimeter 54 of selected portion 52. In a particular embodiment, tweezers are used to manually peel separated organic film 60 from the surface of substrate 50 and to remove separated organic film 60 from substrate 50.

Thus, method 400 represents a series of steps for removing organic film 60 from selected portion 52 of substrate 50. Method 400 represents an example of one mode of operation, and system 10 includes components with capabilities suitable for performing this method of operation. Certain steps may take place simultaneously and/or in a different order than shown. In addition, system 10 may use methods with additional or fewer steps for removing organic film 60 from substrate 50, so long as the method remains appropriate.

Although several embodiments have been explicitly described, a plenitude of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. A method of removing an organic film from a selected portion of an implantable medical device, comprising:
    using an infrared laser set at a first value for an operational parameter, tracing the perimeter of a selected portion of the implantable medical device to ablate an organic film along the perimeter of the selected portion, wherein the organic film comprises a polymer bonded to the implantable medical device with a primer compound and the polymer substantially transmits infrared radiation;
    using an infrared laser set at a second value for the operational parameter, scanning the selected portion of the implantable medical device to heat the surface of the device within the perimeter of the selected portion and thereby separate the organic film from the surface of the device within the perimeter of the selected portion; and
    mechanically removing the chemically separated organic film from the surface of the implantable medical device within the perimeter of the selected portion of the device to expose the selected portion.

2. The method of claim 1, wherein the polymer is a polymer of para-xylylene and the primer compound is a silane primer.

3. The method of claim 2, wherein the silane primer comprises gamma-methacryloxypropyltrimethoxysilane and the polymer of para-xylylene comprises poly-monochloro-para-xylylene.

4. The method of claim 1, wherein:
    the operational parameter comprises pulse frequency;
    the first value comprises a pulse frequency between approximately 11 kilohertz and approximately 25 kilohertz; and
    the second value comprises a pulse frequency between approximately 25 kilohertz and approximately 60 kilohertz.

5. The method of claim 1, further comprising using a processor to access data stored in a memory defining the perimeter of the selected portion of the implantable medical device.

6. The method of claim 1, further comprising storing a plurality of data sets each corresponding to a different implantable medical device, each data set comprising the first and second values for the operational parameter for removing an organic film from a selected portion of a corresponding implantable medical device.

7. The method of claim 1, further comprising, using a laser set at a third value for the operational parameter, scanning the selected portion of the implantable medical device to clean the surface of the device within the perimeter of the selected portion.

8. The method of claim 7, wherein:
the operational parameter comprises pulse frequency;
the first value comprises a pulse frequency between approximately 11 kilohertz and approximately 25 kilohertz;
the second value comprises a pulse frequency between approximately 25 kilohertz and approximately 60 kilohertz; and
the third value comprises a pulse frequency between approximately 25 kilohertz and 35 kilohertz.

* * * * *